(12) United States Patent
Richmond et al.

(10) Patent No.: US 11,474,041 B2
(45) Date of Patent: Oct. 18, 2022

(54) SENSOR FOR MONITORING THE PHYSICAL STATE OF A VEHICLE OCCUPANT

(71) Applicant: Aptiv Technologies Limited, St. Michael (BB)

(72) Inventors: Zachary J. Richmond, Warren, OH (US); Evangelia Rubino, Warren, OH (US); Robert J. Seidler, Warren, OH (US)

(73) Assignee: APTIV TECHNOLOGIES LIMITED

( * ) Notice: Subject to any disclaimer, the term of this patent is extended or adjusted under 35 U.S.C. 154(b) by 0 days.

(21) Appl. No.: 17/241,155

(22) Filed: Apr. 27, 2021

(65) Prior Publication Data

US 2021/0255108 A1    Aug. 19, 2021

Related U.S. Application Data

(60) Continuation of application No. 16/542,900, filed on Aug. 16, 2019, now Pat. No. 10,801,963, which is a division of application No. 15/490,289, filed on Apr. 18, 2017, now Pat. No. 10,377,386.

(51) Int. Cl.
*G01J 3/44* (2006.01)
*G01N 21/65* (2006.01)
*G01N 21/01* (2006.01)

(52) U.S. Cl.
CPC .............. *G01N 21/65* (2013.01); *G01N 21/01* (2013.01); *G01N 2201/129* (2013.01); *G01N 2201/13* (2013.01)

(58) Field of Classification Search
CPC .................. G01N 21/65; G01N 21/658; G01N 2021/656; G01J 3/44; G01J 3/02

USPC ........................................................ 356/301
See application file for complete search history.

(56) References Cited

U.S. PATENT DOCUMENTS

| 5,214,503 | A | 5/1993 | Chiu et al. |
| H1599 | H | 10/1996 | Task |
| 9,603,560 | B2 | 3/2017 | Monty et al. |
| 9,751,534 | B2 * | 9/2017 | Fung ........................ G07C 5/02 |
| 2003/0218676 | A1 | 11/2003 | Miyahara |
| 2006/0088298 | A1 | 4/2006 | Frame et al. |
| 2012/0147243 | A1 | 6/2012 | Townsend et al. |
| 2013/0087180 | A1 | 4/2013 | Stark et al. |
| 2015/0201837 | A1 | 7/2015 | Song et al. |

(Continued)

FOREIGN PATENT DOCUMENTS

WO      2016138087 A1    9/2016

OTHER PUBLICATIONS

Self-adhesive epidermal carbon nanotube electronics for tether-free long-term continuous recording of biosignals;Seung Min Lee1 (Year: 2014).*

(Continued)

*Primary Examiner* — Md M Rahman
(74) *Attorney, Agent, or Firm* — Billion & Armitage

(57) ABSTRACT

A sensor configured to determine a physical state of a vehicle occupant within a vehicle includes an electrode containing nanoscale metal fibers. The electrode is located within the vehicle to be in contact with the vehicle occupant. The sensor also includes a controller configured to determine the physical state of the vehicle occupant based on an output of the electrode.

17 Claims, 6 Drawing Sheets

(56) References Cited

U.S. PATENT DOCUMENTS

2016/0082806 A1 3/2016 Park
2016/0118566 A1 4/2016 Lee et al.

OTHER PUBLICATIONS

Thermoelectric "Fabrics" based on carbon nanotube composites, David L. Carroll, Center for Nanotechnology and Molecular Materials, Department of Physics, Wake Forest University, Winston-Salem NC https://energy.gov/sites/prod/files/2014/03/f10/carroll_0.pdf.

"Self-adhesive epidermal carbon nanotube electronics for tether-free long-term continuous recording of biosignals", Seung Min Lee, et al., Aug. 15, 2014, pp. 1-9.

* cited by examiner

SENSOR FOR MONITORING THE PHYSICAL STATE OF A VEHICLE OCCUPANT

CROSS-REFERENCE TO RELATED APPLICATION

This application is a continuation application of co-pending U.S. patent application Ser. No. 16/452,900, filed on Jun. 26, 2019 which is a divisional application of U.S. patent application Ser. No. 15/490,289, now U.S. Pat. No. 10,377,386, filed on Apr. 18, 2017, the entire disclosure of each of which is hereby incorporated by reference.

TECHNICAL FIELD OF THE INVENTION

The invention generally relates to a sensor for monitoring physical state of vehicle driver and passengers having electrodes formed of conductive fabric or film materials containing nanoscale metal fibers or carbon nanotubes.

BACKGROUND OF THE INVENTION

Monitoring of driver awareness and physical state in motor vehicles has been increasing to improve passenger safety. Current monitoring systems typically use cameras as inputs to determine driver awareness based on eye position or facial expression. Monitoring systems based on cameras may be unreliable due to differences in facial expressions between different people and the programming associated with the cameras. Therefore, an improved system for monitoring driver awareness and state remains desired.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

BRIEF SUMMARY OF THE INVENTION

In accordance with an embodiment of the invention, a system configured to determine a physical state of a vehicle occupant within a vehicle is provided. The system includes an electrode containing nanoscale metal fibers or carbon nanotubes and a controller connected to the electrode configured to determine the physical state of the vehicle occupant based on an output of the electrode and further configured initiate a countermeasure based on the physical state of the vehicle occupant. The electrode is in contact with the vehicle occupant, for example the electrode is in contact with the skin surface of the vehicle occupant.

The system may include at least two electrodes that are connected to the controller and comprise nanoscale metal fibers or carbon nanotubes. All of these electrodes are in contact with the vehicle occupant, for example the electrodes are in contact with the skin surface of the vehicle occupant.

The controller may be configured to determine a voltage potential difference between the at least two electrodes and determine a heart rate of the vehicle occupant based on a change in the voltage potential difference between the at least two electrodes. The controller is also configured to initiate the countermeasure if the heart rate is not within a predetermined range. The electrodes may be incorporated into a cloth material forming an interior surface of the vehicle, such as a seat, an arm rest, a head rest, and a seat belt. Alternatively, or in addition, the electrodes may be incorporated into a conductive film material, such as a polymer-based film, forming an interior surface of the vehicle such as a seat, an arm rest, a head rest, a steering wheel, a door panel, a door handle, or a control button. The controller may be further configured to determine a state of alertness of the vehicle occupant based on the heart rate and initiate the countermeasure if the state of alertness is not within a predetermined range. Alternatively, or in addition, the controller may be further configured to determine a presence of the vehicle occupant based on the heart rate and initiate the countermeasure if the controller detects the presence of the vehicle occupant.

Alternatively, or in addition, the controller may be configured to determine a voltage potential difference between the at least two electrodes and determine brain wave activity of the vehicle occupant based on a change in the voltage potential difference between the at least two electrodes. The controller may be further configured to determine the physical state of the vehicle occupant based on the brain wave activity and initiate the countermeasure based on the brain wave activity. The electrodes may comprise a cloth material or a foam material that are incorporated into an item such as a headband, a headrest, a headphone, or a helmet.

The electrode may be configured to detect a concentration level of a substance in sweat of the vehicle occupant. The controller connected to the electrode may be configured to determine the physical state of the vehicle occupant based on the concentration level of the substance in the sweat of the vehicle occupant detected by the electrode and initiate the countermeasure if the concentration level is not within a predetermined range. The electrode may be incorporated into a cloth material forming an interior surface of the vehicle such as a seat, an arm rest, a seat belt, or a head rest. Alternatively, or in addition, the electrode may be incorporated into a conductive film material, such as a polymer-based film, forming an interior surface of the vehicle such as a seat, an arm rest, a head rest, or a seat belt.

In accordance with another embodiment of the invention, a system configured to generate electricity based upon a temperature difference between a vehicle occupant and a portion of a vehicle interior is provided. The system includes a thermoelectric device containing nanoscale metal fibers or carbon nanotubes incorporated into an interior surface of the vehicle and a pair of electrodes connected to the thermoelectric device and the electrical system of the vehicle. The thermoelectric device has a first side that is in contact with the vehicle occupant and a second side opposite the first side that is in contact with the portion of the vehicle interior. The thermoelectric device is configured to supply electrical power to an electrical system of the vehicle.

The thermoelectric device may be incorporated into a cloth material forming the interior surface of the vehicle such as a seat, an arm rest, a head rest, or a seat belt. Alternatively, the thermoelectric device may be incorporated into a conductive film material forming the interior surface of the vehicle such as a seat, an arm rest, a head rest, a steering wheel, a door panel, a door handle, or a control button. The electrical system may be configured to provide the electrical power to the thermoelectric device, thereby heating the portion of the vehicle interior and/or further configured to provide the electrical power to the thermoelectric device having a reversed polarity, thereby cooling the portion of the vehicle interior.

BRIEF DESCRIPTION OF THE SEVERAL VIEWS OF THE DRAWING

The present invention will now be described, by way of example with reference to the accompanying drawings, in which.

In the figures, similar elements of the various embodiments share the last two digits of the reference numbers.

DETAILED DESCRIPTION OF THE INVENTION

A physical state monitoring system that is configured to determine a physical state of a vehicle occupant within a vehicle is presented herein. The system includes electrodes that are formed of carbon nanotubes and/or nanoscale metal fibers. As used herein, nanoscale metal fibers may be nanoscale stainless steel fibers, metal nanowires, and/or nanoscale metal plated carbon fibers, e.g., copper-plated carbon fibers or nickel-plated carbon fibers. As used herein, nanoscale fibers have a diameter between 1 and 100 nanometers while the length of the fibers may exceed 100 nanometers and be in the micron or millimeter range. The electrodes are in contact with the vehicle occupant and, based on the configuration of the electrodes, able to generate a signal that allows a properly configured controller in communication with the electrodes to determine a heart rate of the vehicle occupant, brain wave activity of the vehicle occupant, or concentration of a substance, such as hormones or neurotransmitters in the sweat of the vehicle occupant. Based on the heart rate, brain wave, or concentration data, the controller may then cause the vehicle to take countermeasures to improve the physical state of the vehicle occupant. For example, if the controller detects an elevated heart rate that indicates that the vehicle occupant is stressed, the controller may reduce the volume of the in-vehicle entertainment system or limit and prioritize messages presented to the occupant in order to help reduce stress levels.

Based on the state of the vehicle occupant as determined by the controller based on the output of the electrode(s), the controller may be configured to:

provide an alert for a person unexpectedly left in the vehicle after exiting the vehicle;

provide an alert for a person unexpectedly in the vehicle before entering the vehicle;

determine alertness of the vehicle occupant by monitoring brain wave activity;

determine alertness or mood of the vehicle occupant by monitoring hormone levels;

determine alertness or mood of the vehicle occupant by monitoring neurotransmitter levels;

determine alertness or physical state of the vehicle occupant by monitoring heart rate;

sense the presence of the vehicle occupant by touch;

adjust heating, ventilation and air conditioning system automatically based on sweating of the vehicle occupant; and generate electricity from a temperature difference between the vehicle occupant and the vehicle interior.

The preceding list in not exhaustive and is non-limiting.

The carbon nanotubes and/or nanoscale metal fibers used to form the electrodes may be incorporated into can be applied to the following portions of the vehicle interior:

seat fabrics;
arm rests;
steering wheels;
head rests;
door handles;
seat belts;
baby/child seats;
control buttons;
wrist bands;
headsets;
headbands;
skin patches; and
helmet like headrest with foam electrodes.

The preceding list in not exhaustive and is non-limiting.

Figure 1:
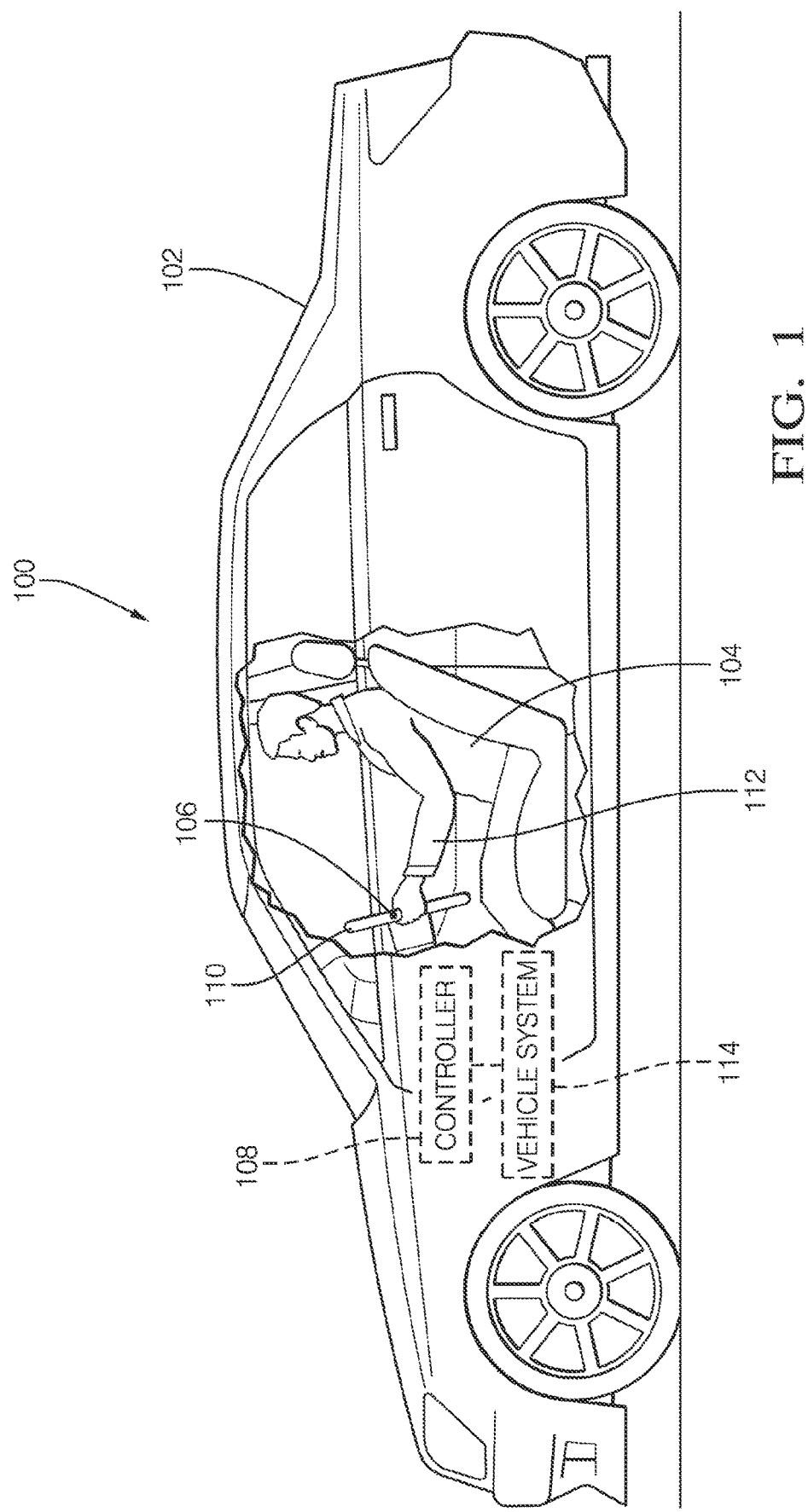
FIG. 1 is a schematic view of a physical state monitoring system for a vehicle occupant in accordance with a first embodiment of the invention.
Figure 2:
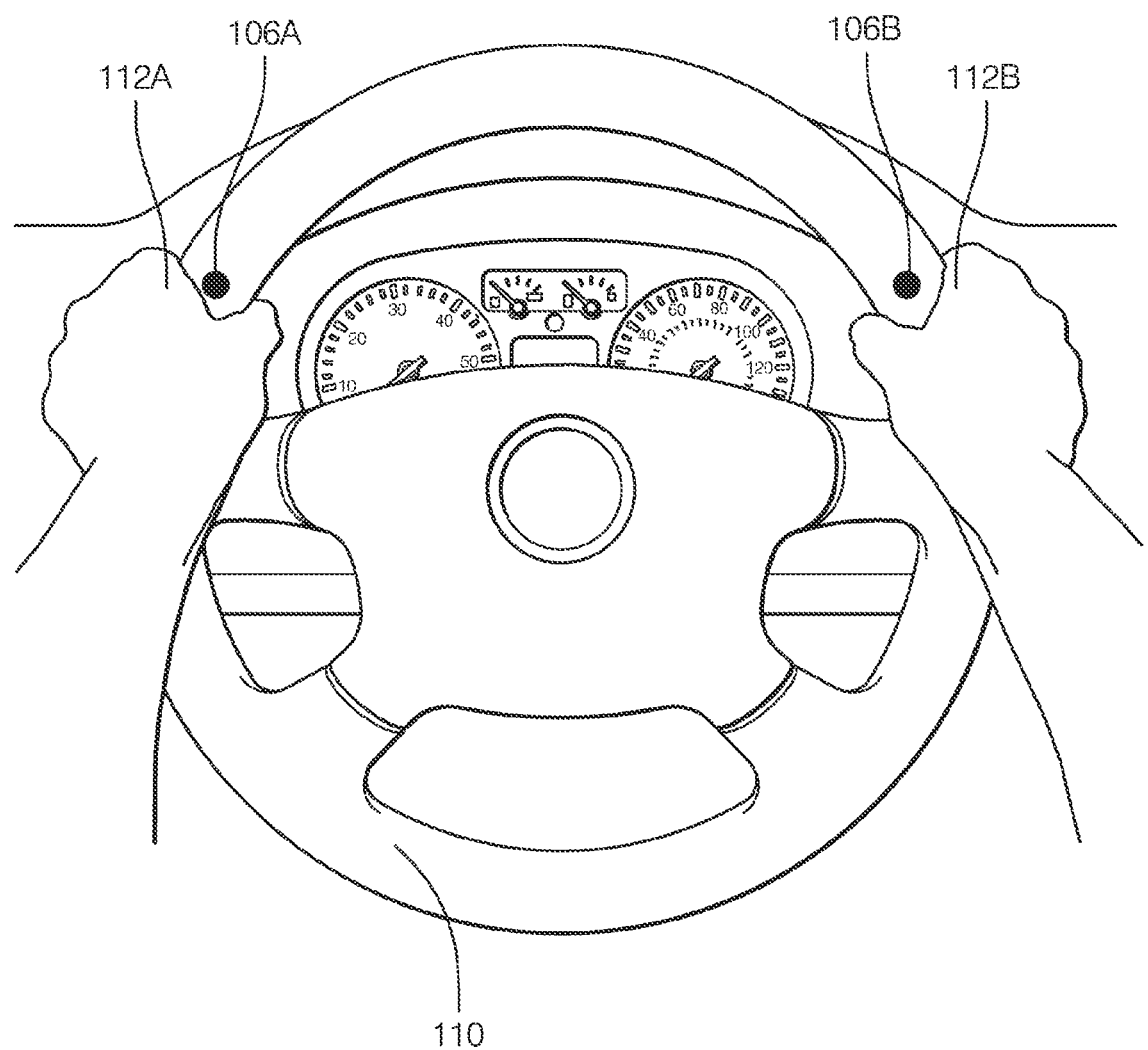
FIG. 2 is a front view of a steering wheel with electrodes of the physical state monitoring system of FIG. 1 in accordance with the first embodiment of the invention.

FIGS. 1 and 2 illustrate a non-limiting example of a physical state monitoring system 100. The system 100 is incorporated into a motor vehicle 102 such as an automobile, light truck, or commercial vehicle. The system is configured to determine a physical state of a vehicle occupant 104. The system includes pair of electrodes 106 that are interconnected to a controller 108 that is configured to determine a voltage difference between the electrodes 106.

As used herein, a controller includes a central processing unit (not shown) that may be a microprocessor, application specific integrated circuit (ASIC), or built from discrete logic and timing circuits. Software instructions that program the controller may be stored in a non-volatile (NV) memory device (not shown). The NV memory device may be contained within the microprocessor or ASIC or it may be a separate device. Non-limiting examples of the types of NV memory that may be used include electrically erasable programmable read only memory (EEPROM), masked read only memory (ROM), and flash memory. The controller may also include a wired transceiver (not shown), such as a controller area network (CAN) transceiver, to allow the controller to establish electrical communication with other vehicle systems.

The controller may also include analog to digital (A/D) convertor circuitry (not shown) to convert voltages from the electrodes to digital information. Alternatively, the A/D convertor circuits may be incorporated into the electrodes. The electrodes may be interconnected to the controller via a hard-wired connection or a wireless connection.

The electrodes 106 connected to the controller 108 are formed from nanoscale metal fibers or carbon nanotubes that are incorporated into a conductive film material, such as a polymer-based film. This film material may be a separate film applied to a vehicle 102 interior surface or may be integral to an exterior layer of the vehicle 102 interior surface. All of these electrodes 106 are in contact with the vehicle occupant 104, for example the electrodes 106 are in contact with the skin surface of the vehicle occupant 104. As shown in FIG. 2, the electrodes 106 are placed on the steering wheel 110 of the vehicle 102 in a location in which the skin of the vehicle occupant's hands 112 would normally be in contact with the electrodes (10 o'clock and 2 o'clock positions).

Without subscribing to any particular theory of operation, as a heart beats, it produces electrical activity that cause changes in voltage potential in the skin. The voltage potential at various locations on the body, e.g., left hand 112A and right hand 112B, change as the various chambers of the heart contract in sequence. One of the electrodes 106A on the steering wheel 110 is normally in contact with the left hand 112A and the other electrode 106B is in contact with the right hand 112B. The controller 108 is configured to determine the voltage potential difference between the two electrodes 106 and determine the heart rate of the vehicle occupant 104 based on a change in the voltage potential difference between the electrodes 106. The controller 108 is also configured to cause the vehicle system 114 initiate the countermeasure if the heart rate is not within a predetermined range, e.g., a heart rate above 120 beats per minute (BPM) may indicate that the vehicle occupant 104 is stressed. The predetermined range may be reconfigurable to accommodate the physiology of a particular vehicle occupant 104.

The controller 108 may be further configured to determine a state of alertness of the vehicle occupant 104 based on the heart rate. Studies have shown a correlation the state of alertness and heart rate, specifically a higher state of alertness is correlated with a higher heart rate. If the detected heart rate falls into a range associated with a low level of alertness, the controller 108 may initiate a countermeasure in a vehicle system 114, such as commanding the heating, ventilation, and air conditioning (HVAC) system to reduce the temperature in the vehicle interior.

The controller 108 may be further configured to determine a presence of the vehicle occupant 104 in the based on the detection of a heart rate when such an occupant would not be expected, for example a child remaining in the vehicle 102 when the vehicle 102 is turned off and locked. The controller 108 may then cause the vehicle system 114 to initiate the countermeasure, such as such as generating an alarm to alert a responsible authority and/or activate the HVAC system bring the temperature within the passenger compartment to a safe level.

Alternative embodiments of the invention in which the electrodes are incorporated into interior surfaces of the vehicle, such as a seat, headrest, or seat belt may also be envisioned.

Figure 3:
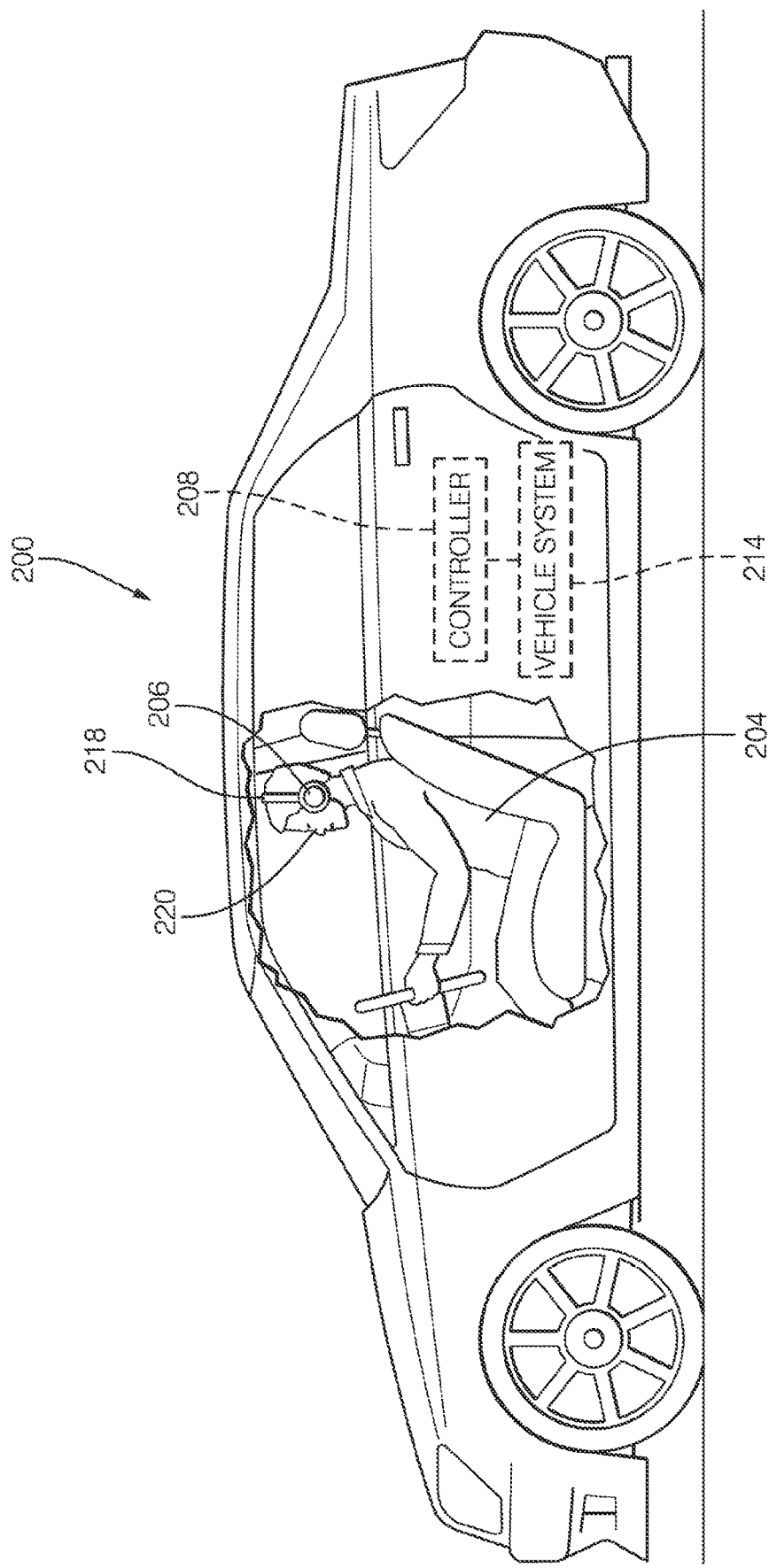
FIG. 3 is a schematic view of a physical state monitoring system for a vehicle occupant in accordance with a second embodiment of the invention.
Figure 4:
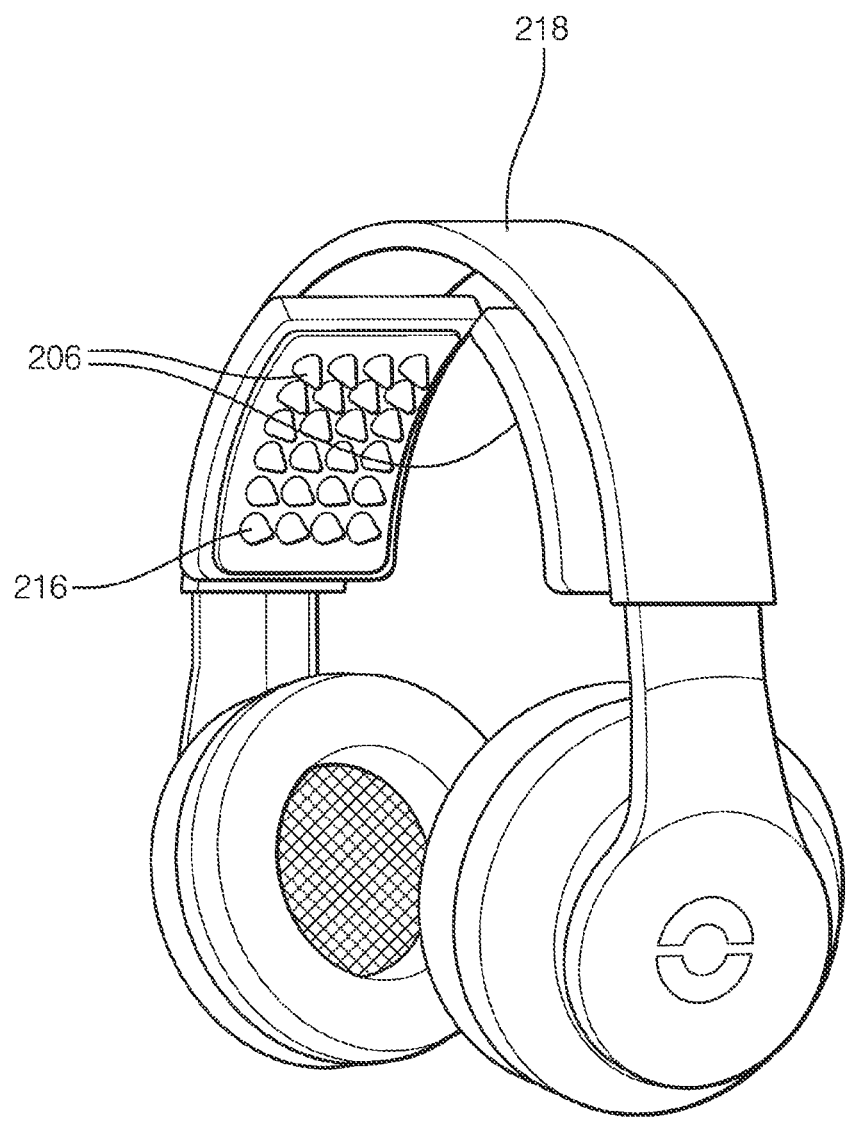
FIG. 4 is a perspective view of headphones with electrodes of the physical state monitoring system of FIG. 3 in accordance with the second embodiment of the invention.

FIGS. 3 and 4 illustrate another non-limiting example of a physical state monitoring system 200. The controller 208 in this system 200 is configured to determine a voltage potential difference between two electrodes 206 formed from nanoscale metal fibers or carbon nanotubes and determine brain wave activity of the vehicle occupant 204 based on a change in the voltage potential difference between the two electrodes 206. The controller 208 is further configured to determine the physical state of the vehicle occupant 204 based on the brain wave activity and cause a vehicle system 214 to initiate the countermeasure based on the brain wave activity. As shown in FIG. 4, the electrodes 206 that are formed of carbon nanotubes, nanoscale stainless steel fibers, metal nanowires, and/or nanoscale metal plated carbon fibers, e.g., copper-plated carbon fibers or nickel-plated carbon fibers are incorporated in a polymeric foam material 216 and contained in a headset 218 that is in contact with the vehicle occupant's head 220. Alternative embodiments of the system 200 may be envisioned in which the electrodes 206 are incorporated into a cloth material and contained in an item such as a headband, a headrest, or a helmet.

Figure 5:
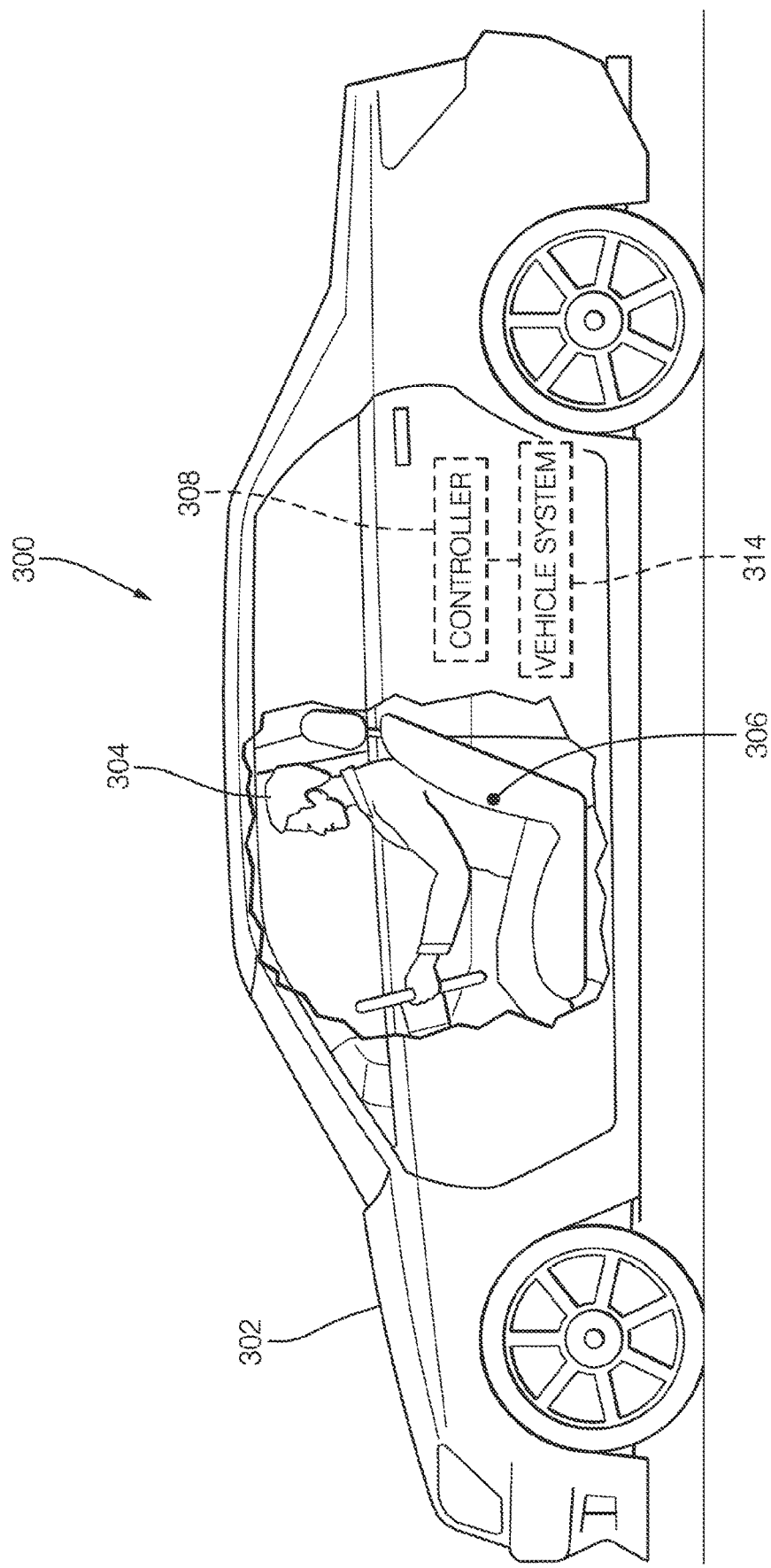
FIG. 5 is a schematic view of a physical state monitoring system for a vehicle occupant in accordance with a third embodiment of the invention.

FIG. 5 illustrates yet another non-limiting example of a physical state monitoring system 300. This system 300 includes an electrode 306 formed from nanoscale metal fibers or carbon nanotubes that is configured to detect a concentration level of a substance, such as a hormone or neurotransmitter, in sweat of the vehicle occupant 304. The controller 308 connected to the electrode 306 may be configured to detect the determine the concentration level of a substance based upon the output of the electrode 306 and determine the physical state of the vehicle occupant 304 based on the concentration level of the substance. The controller 308 will then instruct the vehicle system 314 to initiate the countermeasure if the concentration level is not within a predetermined range. The electrode 306 may be configured to detect a hormone associated with stress, such as cortisol, and the controller 308 will then initiate a countermeasure to reduce stress if the level detected by the controller 308 exceeds the predetermined limit. The electrode 306 may alternatively configured to detect a hormone, such as insulin that is indicative of the health of the vehicle occupant 304. If the inulin level determined by the controller 308 is outside the predetermined range, the controller 308 may command the vehicle system 314 to initiate a safety countermeasure, such as commanding the vehicle's telematics system to issue an emergency call to an emergency response center. In the illustrated example, the electrode 306 is incorporated into a cloth material forming an interior surface of the vehicle 302 that is in contact with a portion of the vehicle occupant 304 that is prone to sweating, such as a seat, an arm rest, a seat belt, or a head rest. Alternatively, or in addition, the electrode 306 may be incorporated into a conductive film material, such as a polymer-based film, forming an interior surface of the vehicle 302 such as a seat, an arm rest, a head rest, or a seat belt. The seat or steering wheel may contain a heating circuit (not shown) that is periodically activated by the controller 308 to cause the vehicle occupant 304 to produce sweat that may be analyzed by the system 300.

Figure 6:
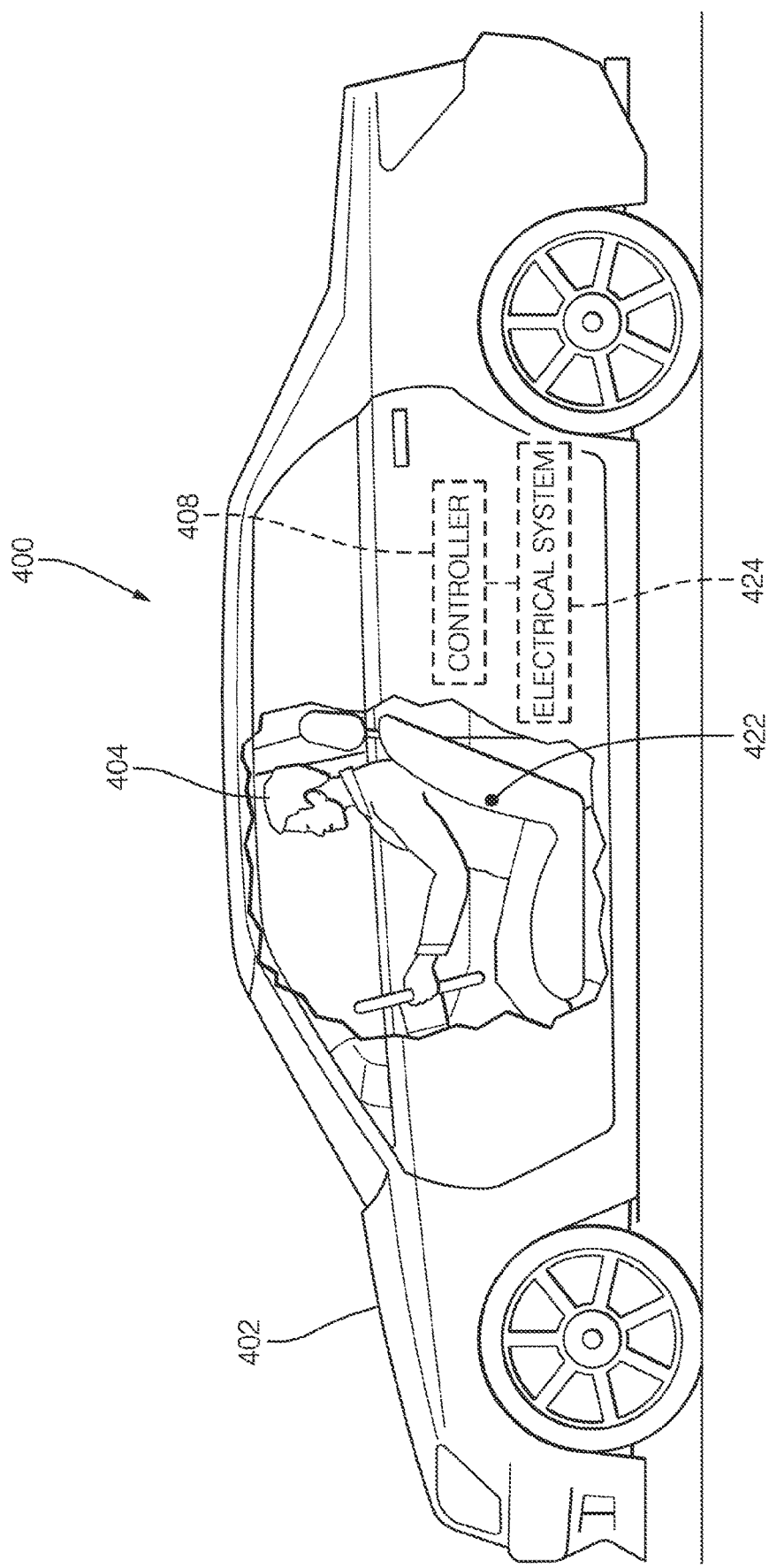
FIG. 6 is a schematic view of a thermoelectric generator system for a vehicle in accordance with a fourth embodiment of the invention.

FIG. 6 illustrates a non-limiting example of a thermoelectric generator system 400 that is configured to generate electricity based upon a temperature difference between a vehicle occupant 404 and a portion of a vehicle interior. This system 400 includes a thermoelectric device 422 containing nanoscale metal fibers or carbon nanotubes that is incorporated into an interior surface of the vehicle 402 and connected to the electrical system 424 of the vehicle 402. The thermoelectric device 422 has a first side that is in contact with the vehicle occupant 404 and a second side that is in contact with the portion of the vehicle interior. The thermoelectric device 422 is configured to supply electrical power to the electrical system 424 of the vehicle 402.

The thermoelectric device 422 is incorporated into a cloth material forming the interior surface of the vehicle 402 such as a seat, an arm rest, a head rest, or a seat belt. Alternatively, the thermoelectric device 422 may be incorporated into a conductive film material forming the interior surface of the vehicle 402 such as a seat, an arm rest, a head rest, a steering wheel, a door panel, a door handle, or a control button. The system 400 may include a controller 408 that configures the electrical system 424 to provide electrical power to the thermoelectric device 422, thereby heating the portion of the vehicle interior. The controller 408 may further configure the electrical system 424 to provide electrical power to the thermoelectric device 422 having a reversed polarity, thereby cooling the portion of the vehicle interior.

Accordingly, a system 100, 200, 300 configured to monitor a physical state of a vehicle occupant within a vehicle is provided. These physical state monitoring systems include electrodes that are formed of nanoscale metal fibers or carbon nanotubes that are incorporated into cloth materials or conductive films forming interior surfaces of the vehicle such as seat fabrics, arm rests, steering wheels, head rests, door handles, seat belts, baby/child seats, and/or control buttons. These physical state monitoring systems determine the physical state of a vehicle occupant based on heart rate, brain wave activity, or secreted hormone/neurotransmitters. A system 400 for generating electricity based upon a temperature difference between a vehicle occupant and a portion of a vehicle interior is also provided. This system 400 includes a thermoelectric device that is also formed of nanoscale metal fibers or carbon nanotubes that are incorporated into cloth materials or conductive films forming interior surfaces of the vehicle such as seat fabrics, arm rests, steering wheels, head rests, door handles, seat belts, baby/child seats, and/or control buttons.

While this invention has been described in terms of the preferred embodiments thereof, it is not intended to be so limited, but rather only to the extent set forth in the claims that follow. Moreover, the use of the terms first, second, etc. does not denote any order of importance, but rather the terms first, second, etc. are used to distinguish one element from another. Furthermore, the use of the terms a, an, etc. do not denote a limitation of quantity, but rather denote the presence of at least one of the referenced items. Additionally, directional terms such as upper, lower, etc. do not denote any particular orientation, but rather the terms upper, lower, etc. are used to distinguish one element from another and locational establish a relationship between the various elements.

We claim:

1. A sensor configured to determine a physical state of a vehicle occupant within a vehicle, comprising:
    at least two electrodes containing nanoscale metal fibers and configured to be placed in a location in the vehicle where the at least two electrodes are in contact with a skin surface of the vehicle occupant; and
    a controller connected to the at least two electrodes and configured to determine the physical state of the vehicle occupant based on an output of the at least two electrodes.

2. The sensor according to claim 1, wherein the nanoscale metal fibers are selected from a list consisting of stainless steel fibers, metal nanowires, metal plated carbon fibers, copper-plated carbon fibers, and nickel-plated carbon fibers.

3. The sensor according to claim 1, wherein the controller is configured to determine a voltage potential difference between the at least two electrodes and wherein the controller is configured to determine a heart rate of the vehicle occupant based on a change in the voltage potential difference between the at least two electrodes.

4. The sensor according to claim 3, wherein the at least two electrodes are incorporated into a conductive film material forming an interior surface of the vehicle.

5. The sensor according to claim 4, wherein the conductive film material is a polymer-based film.

6. The sensor according to claim 3, wherein the controller is further configured to initiate a countermeasure based on the heart rate of the vehicle occupant.

7. The sensor according to claim 6, wherein the controller is further configured to initiate the countermeasure if the heart rate is not within a predetermined range.

8. The sensor according to claim 6, wherein the controller is further configured to determine a state of alertness of the vehicle occupant based on the heart rate and initiate the countermeasure if the state of alertness is not within a predetermined range.

9. The sensor according to claim 6, wherein the controller is further configured to determine a presence of the vehicle occupant based on the heart rate and initiate the countermeasure if the controller detects the presence of the vehicle occupant.

10. The sensor according to claim 6, wherein the countermeasure includes providing an alert for a person unexpectedly left in the vehicle after exiting the vehicle.

11. The sensor according to claim 10, wherein the countermeasure includes activating a heating, ventilation, and air conditioning (HVAC) system to bring a temperature within a passenger compartment to a safe level.

12. The sensor according to claim 6, wherein the countermeasure includes providing an alert for a person unexpectedly in the vehicle before entering the vehicle.

13. The sensor according to claim 6, wherein the countermeasure includes commanding an HVAC system to reduce a temperature in the vehicle interior.

14. The sensor according to claim 6, wherein the countermeasure includes generating an alarm to alert a responsible authority.

15. The sensor according to claim 1, wherein the controller is configured to determine a voltage potential difference between the at least two electrodes, wherein the controller is configured to determine brain wave activity of the vehicle occupant based on a change in the voltage potential difference between the at least two electrodes, and wherein the controller is configured to determine the physical state of the vehicle occupant based on the brain wave activity.

16. The sensor according to claim 15, wherein the controller is further configured to determine alertness of the vehicle occupant based on the brain wave activity of the vehicle occupant.

17. The sensor according to claim 15, wherein the controller is further configured to initiate a countermeasure based on the brain wave activity of the vehicle occupant.

* * * * *